US006534572B1

(12) United States Patent
Ahmed et al.

(10) Patent No.: US 6,534,572 B1
(45) Date of Patent: *Mar. 18, 2003

(54) COMPOSITIONS COMPRISING A THERMOPLASTIC COMPONENT AND SUPERABSORBENT POLYMER

(75) Inventors: Sharf U. Ahmed, Woodbury, MN (US); Andualem W. Emiru, Woodbury, MN (US); Leslie J. Clapp, Wyoming, MN (US); Mark S. Kroll, Arden Hills, MN (US)

(73) Assignee: H. B. Fuller Licensing & Financing, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/306,265

(22) Filed: May 6, 1999

Related U.S. Application Data

(60) Provisional application No. 60/084,582, filed on May 7, 1998.

(51) Int. Cl.⁷ ................................................ C08L 91/06
(52) U.S. Cl. ...................... 524/275; 523/105; 523/111; 524/277; 524/500; 428/467
(58) Field of Search ................. 524/500, 502, 524/762, 772, 275, 916, 272; 428/467; 442/41, 84, 90

(56) References Cited

U.S. PATENT DOCUMENTS

| 3,615,106 A | * | 10/1971 | Flanagan et al. ............ 524/272 |
| 3,972,328 A |   | 8/1976  | Chen |
| 4,166,051 A |   | 8/1979  | Cilento et al. |
| 4,192,785 A |   | 3/1980  | Chen et al. |
| 4,231,369 A |   | 11/1980 | Sorensen et al. |
| 4,367,732 A |   | 1/1983  | Poulsen et al. |
| 4,378,018 A |   | 3/1983  | Alexander et al. |
| 4,392,908 A |   | 7/1983  | Dehnel |
| 4,393,080 A |   | 7/1983  | Pawelchak et al. |
| 4,477,325 A |   | 10/1984 | Osburn |
| 4,551,490 A |   | 11/1985 | Doyle et al. |
| 4,588,767 A | * | 5/1986  | Schoenberg et al. ........ 524/272 |
| 4,837,077 A |   | 6/1989  | Anton et al. |
| 4,855,335 A |   | 8/1989  | Neperud |
| 4,977,211 A |   | 12/1990 | Doi et al. |
| 5,234,986 A | * | 8/1993  | McBride .................... 524/505 |
| 5,246,770 A |   | 9/1993  | Bottiglione et al. |
| 5,248,709 A |   | 9/1993  | Brehm |
| 5,252,646 A | * | 10/1993 | Iovine et al. ................ 524/270 |
| 5,356,963 A | * | 10/1994 | Kauffman et al. ........... 524/43 |
| 5,567,744 A | * | 10/1996 | Nagata et al. .............. 523/200 |
| 5,686,515 A | * | 11/1997 | Phillips et al. ............. 524/275 |
| 6,087,550 A | * | 7/2000  | Anderson-Fischer et al. .... 604/364 |
| 6,103,809 A | * | 8/2000  | Ahmed et al. .............. 524/489 |

FOREIGN PATENT DOCUMENTS

| JP | 60-195299  | 10/1985 |
| JP | 08027372   | 7/1994  |
| JP | 97176618   | 7/1997  |
| WO | WO 91/18042 | 11/1991 |
| WO | WO 98/27559 | 6/1998  |

* cited by examiner

*Primary Examiner*—Edward J. Cain
*Assistant Examiner*—Wyrozebski Lee

(57) ABSTRACT

The present invention relates to a composition comprising a thermoplastic component and at least one superabsorbent polymer, methods of use for such composition, and articles comprising such composition. The composition may be formed into a film layer or applied to an article with various hot melt adhesive application techniques. The composition is useful for a variety of end-uses, particularly for use in disposable absorbent articles such as disposable diapers, feminine napkins and medical dressings.

24 Claims, No Drawings

COMPOSITIONS COMPRISING A THERMOPLASTIC COMPONENT AND SUPERABSORBENT POLYMER

RELATED APPLICATIONS

This application is a Continuation-In-Part of U.S. patent application Ser. No. 60/084,582 filed May 7, 1998.

FIELD OF THE INVENTION

The present invention relates to a composition comprising a thermoplastic component and at least one superabsorbent polymer, methods of use for such composition, and articles comprising such composition. The composition may be formed into a film layer or applied to an article with various hot melt adhesive application techniques. The composition is useful for a variety of end-uses, particularly for use in disposable absorbent articles such as disposable diapers, feminine napkins and medical dressings.

BACKGROUND OF THE INVENTION

Water-insoluble, water swellable hydrogel-forming absorbent polymers, also referred to as superabsorbent polymers (SAP), are capable of absorbing large quantities of liquids such as water, body fluids (e.g., urine, blood), industrial fluids, household fluids and are further capable of retaining such absorbed liquids under moderate pressures.

For example, SAP is employed in various cable applications to shield the penetration of moisture. When the outer sheath of the cable is damaged allowing penetration of fluids, the SAP absorbs the incoming liquid and swells, forming a physical barrier to the entry of any further fluid. Particulate SAP is typically held in place by means of a hydrosoluble binder. For example, U.S. Pat. No. 4,837,077 issued to Anton et al., Jun. 6, 1989, relates to a hydroexpansible composite material including a solid flat support having on at least one of its faces a coating with a high proportion of a hydroexpansible polymer powder fixed to the support by means of a hydrosoluble binder, the coating being essentially formed of 95% to 55% by weight of a hydroexpansible polymer powder, 5% to 23% by weight of a hydrosoluble binder, and surfactant in a positive amount of up to 22% by weight. The ingredients are homogenized by means of a liquid. This reference expressly teaches that thermoplastic substances cause an unfavorable effect, the blockage of a part of the hydroexpansible polymer powder, thus limiting its ability to swell in the presence of water.

The absorption characteristics of SAP materials make them especially useful for incorporation into absorbent articles such as disposable diapers, adult incontinent pads and briefs, and catamenial products such as sanitary napkins and the like. A desired characteristic of such disposable absorbent articles is thinness. Thinner disposable articles are less bulky to wear, better fitting under clothing and are less noticeable. Further, thin disposable absorbent articles are more compact, making the product easier for the consumer to carry and store. Compactness in packaging also results in reduced distribution costs for the manufacturer and the distributor, including less shelf space. The ability to provide thinner absorbent articles such as a diaper has been contingent on the ability to develop relatively thin absorbent cores or structures that can acquire and store large quantities of fluid, particularly urine. Therefore, there is a trend towards employing higher concentrations of SAP polymers to achieve this purpose.

SAP is typically available in a particulate or powder form that is sprinkled or sifted into the absorbent core portion, which is sandwiched between a fluid pervious topsheet and a fluid impervious backsheet. The incorporation of particulate SAP into an article tends to generate dust from the SAP fines. Further, conventional absorbent articles have the limitation that the absorbent gelling particles are not immobilized and are free to migrate and shift during the manufacturing process and/or use. Movement of the SAP particles during manufacture can lead to absorbent material handling losses during manufacturing operations as well as improper distribution of the particles.

Other problems occur when these absorbent gelling particles migrate during and after swelling. The inability to fix the particles at optimum locations leads to insufficient fluid storage in one area and over-capacity in other areas due to the movement of the SAP particles to locations other than where originally positioned. Another important factor that has to be considered is the liquid permeability of the SAP. It has been discovered that the fluid transport properties of the gel layer formed as a result of the swelling SAP particles in the presence of fluids is extremely important. Although the formation of a SAP gel layer fluid barrier, known as "gel blocking" is desirable for some applications, such as for use in cables, the formation of gel layers in disposable absorbent products is undesirable since it greatly reduces the efficiency of the SAP. Thus, the advantages of being able to fixate SAP in place are apparent and several ways of accomplishing such have been suggested.

For example, U.S. Pat. No. 4,392,908 issued to Dehnel Jul. 12, 1983, concerns a process for manufacturing a water-absorbent article in which particles of a water swellable polymer are fixed to a water-absorbent substrate. The process includes the steps of forming on the surface of water-swellable particles a coating of a thermoplastic adhesive resin; locating the coated particles in their unswollen state and dry state on or within the water-absorbent substrate also in the dry state; and applying heat to soften the thermoplastic coating of the particles and pressing the particles and substrate to cause the particles to be bound to the substrate. The particles of absorbent material can be coated by mixing the absorbent particle with an aqueous latex of the resin and then drying the mixture, spraying a resin solution or latex onto the particles, adding the resin to the particles when the particles are in a slurry, or incorporating the thermoplastic as a solution or latex during the manufacture of the absorbent material.

Further, SAP particles may be combined with certain thermoplastic compositions.

U.S. Pat. No. 4,977,211 issued to Doi, Dec. 11, 1990, teaches a moldable water-absorptive resin composition which comprises (A) 5% to 95% by weight of a water-absorptive resin and 95% to 5% by weight of (B) a polyolefin resin and (C) an ethylene/alpha-olefin copolymer rubber based on the total content of said components (A), (B) and (C), wherein the contents of (C) amounts to 20% to 80% by weight based on the total contents of said component (B) and (C). An ethylene/vinyl acetate copolymer is exemplified having a vinyl acetate content of 33% by weight and a melt index of 30 g/10 min. Subsequently, the water-absorptive resin composition of the present invention can be molded into a form suitable for its final use. The molded products may be subjected to a secondary molding treatment such as foaming or orientation. The compositions can be molded alone into a film, a sheet, fibers or other products.

Japanese Patent Application 9-176618 published Jul. 8, 1997 relates to a water-swelling hot melt presealant for lap joint construction external wall material. The composition includes 20 wt-% to 50 wt-% thermoplastic elastomer, 5 wt-% to 40 wt-% tackifier, 10 wt-% to 50 wt-% plasticizer and 5 wt-% to 35 wt-% water swellable resin. The plasticizer is described as paraffin type oil, naphthene type oil, aromatic type oil, polybutene liquid rubber, polyisobutylene liquid rubber, polyisoprene liquid rubber and its hydrogenated product.

Japanese Patent Application 60-195299, published Oct. 3, 1985 pertains to a method for preventing water leaks with good operability, especially in engineering work and construction employing a water-swellable composition styrene elastomers, highly water absorbing materials and tackifiers. The proportions of the ingredients are usually 5–100 parts of the highly water-absorbing resin and 100 to 200 parts of tackifier based on 100 parts of the styrene elastomer.

More recently, WO 98/27559A1, published Jun. 25, 1998 concerns a water swellable thermoplastic compound for gluing and coating made from a water insoluble component, a water soluble or water dispersible component, and a water-swellable component. Examples of suitable water-soluble or water dispersible oligomers, homopolymer or copolymers include polyethylene glycol in the molecular weight range between 2400 and 20,000, polyvinyl methyl ether, polyvinylpyrrolidone, copolymers of vinyl methyl ether or vinyl pyrrolidone, polyvinyl alcohols, water soluble or water dispersible polyesters or copolyesters, and water soluble or water dispersible acrylate polymers.

SUMMARY OF THE INVENTION

The present inventors have discovered that the inclusion of water soluble or dispersible polymers disadvantageously reduces the rate of fluid acquisition. It is surmised that water soluble/dispersible polymers compete with the SAP in absorption of the fluid. In such instances, the water soluble or dispersible ingredient forms a solution or dispersion that thickens the fluid intended to be absorbed by the SAP. The thickened fluid tends to be absorbed by the SAP at a much slower rater than that of the fluid prior to thickening, thus hindering the rate of absorption.

Surprisingly, the present applicants have found that the fluid acquisition rate and the total absorption capacity for small particle size SAP is not impaired by being admixed with certain thermoplastic compositions. Further, in many instances the presence of the thermoplastic component actually enhances the performance of the SAP, particularly for reducing unintended gel blocking.

The present invention is a composition comprising a thermoplastic composition, also referred to as the "thermoplastic component" and at least one superabsorbent polymer. The thermoplastic component is sufficiently polar and simultaneously of relatively low cohesive strength. The cohesive strength corresponds to the melt index of a polymer or molten viscosity of a mixture of a thermoplastic polymer and other ingredients.

In one embodiment, the present invention is a thermoplastic composition comprising a thermoplastic component comprising at least one thermoplastic polymer and at least one water insoluble diluent having polar functionality and at least one superabsorbent polymer. The thermoplastic component is preferably water insoluble. The diluent is preferably a plasticizer employed at a concentration ranging from about 10 wt-% to about 30 wt-% of the total weight of the composition.

In another embodiment, the present invention is a thermoplastic composition comprising a thermoplastic component comprising at least one interpolymer of ethylene. The interpolymer has a melt index greater than about 500 g/10 min., preferably about 800 g/10 min. and greater, and more preferably about 1000 g/10 min. and greater. Further, the interpolymer of ethylene preferably has a comonomer content of greater than 25 wt-% and preferably greater than about 28 wt-% or higher. The comonomer is preferably vinyl acetate, methacrylate, n-butyl acrylate and mixtures thereof. Further, the composition is preferably free of water soluble/dispersible polymers having a molecular weight (Mw) of greater than 2000.

In another embodiment, the present invention is a thermoplastic composition comprising about 25 wt-% to about 50 wt-% of a thermoplastic component having a viscosity of less than about 30,000 cPs at 177° C. and 50 wt-% to about 75 wt-% of a superabsorbent polymer.

The thermoplastic component may be a single thermoplastic polymer or a blend of thermoplastic polymers in its entirety. Alternatively, the thermoplastic component may comprise at least one thermoplastic polymer in combination with at least one hot melt adhesive ingredient such as plasticizers, tackifiers and waxes. The thermoplastic component is preferably present in an amount ranging from about 40 wt-% to about 70 wt-%, whereas the superabsorbent polymer is preferably present in an amount ranging from about 30 wt-% to about 60 wt-%. Further, the thermoplastic component preferably comprises at least one thermoplastic polymer including block copolymers, amorphous polyolefins, crystalline polyolefins, interpolymers of ethylene and mixtures thereof.

The composition preferably gels at a rate equal to or faster than that of the SAP polymer alone, particularly when employing SAP having a particle size of less than about 200 microns. The rate of gelation is preferably less than 3 hours, more preferably less than 1 hour and most preferably less than about 30 minutes.

The resulting composition can be used in place of particulate or powdered SAP for any application employing such, avoiding the aforementioned problems. The composition can advantageously be applied to an article by any known hot melt application technique, extruded as a rod, strand or fiber, as well as be formed into a film layer on a substrate, thus providing SAP in a roll good form.

In another embodiment, the invention is film layer disposed on a substrate comprising the inventive thermoplastic mixture. The film layer may be formed by providing a molten mixture of the inventive composition comprising at least one thermoplastic polymer and at least one superabsorbent polymer and forming a substantially continuous film from said molten mixture onto a substrate.

In another embodiment, the invention is a method of applying superabsorbent polymer to a substrate comprising the steps of:

a) providing a molten mixture comprising a thermoplastic composition and at least one superabsorbent polymer; and b) applying said mixture to a substrate.

DETAILED DESCRIPTION OF THE INVENTION

The term "thermoplastic composition" and "thermoplastic component" refers to a composition that is reversibly capable of softening or fusing when heated and hardening again when cooled.

The term "molten" as used herein refers to a flowable or liquified state of matter attained with heat.

The terms "water responsive" and "water sensitive" as used herein refers to ingredients that are soluble or dispersible in an aqueous environment. Aqueous environment includes neutral, basic, acidic and ionic aqueous solutions.

The term "water insensitive" as used herein refers to an ingredient that is soluble in water at a concentration less than 1.0 wt-%, and preferably less than 0.5 wt-%.

The present invention is a composition comprising a thermoplastic composition and at least one super absorbent polymer (SAP). The thermoplastic component provides the thermoplasticity of the SAP containing composition, whereas the SAP polymer provides the fluid absorption capability of the composition. The thermoplasticity allows for a variety of application techniques, such as those employed for hot melt adhesives. The thermoplastic component also solves the gel blocking problem. Gel blocking is the phenomena wherein SAP particles absorb fluid and swell into a gel layer. The gel layer creates a barrier and prevents the migration of fluid to the ungelled SAP particles. Since the thermoplastic component provides a means of separating the individual small particle size SAP particles from each other, each SAP particle can absorb fluid and swell independently, essentially unaffected by neighboring SAP particles. Hence gel blocking is reduced, increasing the rate of absorption of the SAP.

The thermoplastic component is sufficiently polar and simultaneously of relatively low cohesive strength. Both these properties are contributed to by the selection of ingredients employed. The thermoplastic component comprises at least one thermoplastic polymer and at least one water insoluble diluent having polar functionality or at least one interpolymer of ethylene having a melt index greater than about 500 g/10 min and a comonomer content greater than about 25 wt-%, or a thermoplastic composition having a viscosity of less than about 30,000 cPs at 350° F. (177° C.) in combination with at least 50 wt-% superabsorbent polymer. The thermoplastic component is present at a concentration sufficient to form a continuous phase within the mixture. Hence, the concentration of thermoplastic component is dependent on the concentration and particle size of the superabsorbent polymer employed. In general, the thermoplastic component comprises from about 20 wt-% to about 80 wt-%, preferably from about 30 wt-% to about 70 wt-%, and most preferably from about 40 wt-% to about 60 wt-%.

The thermoplastic composition may comprise, in its entirety, a single thermoplastic polymer, a blend of thermoplastic polymers, or alternatively the thermoplastic composition may be a hot melt adhesive comprising at least one thermoplastic polymer in combination with other thermoplastic diluents such as tackifying resins and plasticizers. The invention also contemplates the thermoplastic composition being comprised entirely of at least one thermoplastic tackifier, plasticizer, wax and mixtures thereof. However, in most instances, a thermoplastic polymer is necessary to provide the desired properties, particularly strength. The thermoplastic polymer alone may exhibit sufficient adhesive characteristics for some applications. However, preferably the thermoplastic polymer is combined with tackifiers and plasticizers to modify the adhesive properties for use in the intended application. This embodiment is particularly useful wherein the composition serves a dual purpose of providing the SAP in a non-particulate form as well as fixating the SAP in place. SAP containing hot melt adhesive may also serve the function of bonding at least one substrate layer to at least one other substrate layer.

The thermoplastic component of the present invention typically comprises at least one thermoplastic polymer present in an amount ranging from about 10 wt-% to about 60 wt-%, preferably in an amount ranging from about 15 wt-% to about 50 wt-%, and more preferably in an amount ranging from about 20 wt-% to about 50 wt-%, with respect to the total weight of the composition.

For embodiments that employ only a single thermoplastic polymer as the entire thermoplastic component, the thermoplastic polymer will typically either be sufficiently polar and/or combined with a polar diluent. In the case of employing blends of thermoplastic polymers as the entire thermoplastic component, the blend will exhibit the same desired properties. For some embodiments, a relatively high viscosity thermoplastic polymer is combined with relatively low viscosity thermoplastic components to enhance the cohesive strength of the mixture while maintaining good processability. For this embodiment, the relatively high viscosity polymer generally has a melt index (MI) of about 400 g/10 min. or less preferably about 200 g/10 min. or less, more preferably about 100 g/10 min. or less and most preferably less than about 50 g/10 min. In order to achieve the desired polarity or molten viscosity profile, these relatively high viscosity polymers may only be employed at minimal concentrations, typically in an amount less than about 40 wt-%, preferably from about 5 wt-% to about 30 wt-%, and more preferably from about 10 wt-% to about 25 wt-%, with respect to the total weight of the composition.

Accordingly, a wide variety of thermoplastic polymers are suitable for use in the present invention. Such thermoplastic polymers are preferably water insensitive. Exemplary polymers for use in the invention include styrenic block copolymers, amorphous and crystalline polyolefins including homogeneous and substantially linear ethylene/alpha-olefin interpolymers; interpolymers of ethylene such as ethylene-vinyl-acetate (EVA), ethylene-methyl acrylate (EMA) and ethylene n-butyl acrylate (EnBa); and mixtures thereof.

A wide variety of block copolymers are useful in the present invention including A-B-A triblock structures, A-B diblock structures, (A-B)$_n$ radial block copolymer structures, as well as branched and grafted versions of such, wherein the A blocks are non elastomeric polymer blocks, typically comprising polystyrene, and the B blocks are unsaturated conjugated diene or hydrogenated version thereof. In general, the B block is typically isoprene, butadiene, ethyleneibutylene (hydrogenated butadiene), ethylene/propylene (hydrogenated isoprene), and mixtures thereof. Commercial embodiments include the Kratont® D and G series block copolymers, available from Shell Chemical Company (Houston, Tex.), Europrenet® Sol T block copolymers available from EniChem (Houston, Tex.), Vector® block copolymers available from Exxon (Dexco) (Houston, Tex.), as well as others. Block copolymer based compositions are particularly useful for pressure sensitive adhesive applications which generally employ a relatively low melt index block copolymer (less than 50 g/10 min) in combination with at least one tackifying resin and plasticizing oil.

Amorphous polyolefins or amorphous polyalphaolefms (APAO) are homopolymers, copolymers, and terpolymers of $C_2$–$C_8$ alphaolefins. These materials are typically polymerized by means of processes which employ Ziegler-Natta catalysts resulting in a relatively broad molecular weight distribution. Commercially available amorphous polyalpha-olefins include Rextac® and REXFlex® propylene based homopolymers, ethylene-propylene copolymers and butene-propylene copolymers available from Rexene (Dallas, Tex.) as well as Vestoplast® alpha-olefin copolymers available from Hils (Piscataway, N.J.).

Metallocene polyolefins are homogeneous linear and substantially linear ethylene polymers prepared using single-site or metallocene catalysts. Homogeneous ethylene polymers are characterized as having a narrow molecular weight distribution and a uniform short-chain branching distribution. In the case of substantially linear ethylene polymers, such homogeneous ethylene polymers are further characterized as having long chain branching. Substantially linear ethylene polymers are commercially available from The Dow Chemical Company as Affinity™ polyolefin plastomers, which are produced using Dow's Insite™ technology, whereas homogeneous linear ethylene polymers are available from Exxon Chemical Company under the tradename Exact®g. Homogeneous linear and substantially linear ethylene polymers having a relatively low density, ranging from about 0.855 to about 0.885, and a relatively low melt index, for example less than about 50 g/10 min. are most preferred, particularly for creating elastomeric fibers, films and adhesive compositions that swell upon exposure to water.

The term "interpolymer" is used herein to indicate a copolymer, terpolymer, or higher order polymer. That is, at least one other comonomer is polymerized with ethylene to make the interpolymer. Interpolymers of ethylene are those polymers having at least one comonomer selected from the group consisting of vinyl esters of a saturated carboxylic acid wherein the acid moiety has up to 4 carbon atoms, unsaturated mono- or dicarboxylic acids of 3 to 5 carbon atoms, a salt of the unsaturated acid, esters of the unsaturated acid derived from an alcohol having 1 to 8 carbon atoms, and mixtures thereof.

If employed uncompounded, the ethylene to unsaturated carboxylic comonomer weight ratio is preferably greater than about 3:1, more preferably about 2:1. Hence the comonomer concentration is preferably greater than 30 wt-%, more preferably greater than 33 wt-% and most preferably greater than 35 wt-%, with respect to the total weight of the ethylene interpolymer. The melt index of the interpolymers of ethylene may range from about 50 to about 2000, preferably from about 100 to 1500, more preferably from about 200 to 1200, and most preferably from about 400 to 1200 g/10 min. When employing a polymer having too low of a melt index uncompounded, the strength of the polymer tends to constrain the swelling of the SAP particles. However, as previously discussed, the disadvantages of the lower melt index interpolymers of ethylene can be overcome by formulating the polymer with diluents.

Suitable ethylene/unsaturated carboxylic acid, salt and ester interpolymers include ethylene/vinyl acetate (EVA) ethylene/acrylic acid (EEA) and its ionomers; ethylene/methacrylic acid and its ionomers; ethylene/methyl acrylate (EMA); ethylene/ethyl acrylate; ethylene/n-butyl acrylate (EnBA); as well as various derivatives thereof that incorporate two or more comonomers.

Other suitable thermoplastic polymers that may be employed include polylactide, caprolactone polymers, and poly (hydroxy-butyrate/hydroxyvalerate), certain polyvinyl alcohols, biodegradable copolyesters such as Eastman Copolyester 14766 (Eastman), linear saturated polyesters such as Dynapol or Dynacoll polymers from Hüils, poly (ethylene oxide)polyether amide and polyester ether block copolymers available from Atochem (PeBax) or Hoechst Celanese (Rite-flex) respectively, and polyamide polymers such as those available from Union Camp (Unirez) or Huls (Vestamelt) or EMS-Chemie (Griltex).

Alternatively, water soluble or water dispersible polymer may be employed provided such polymers are combined with water insoluble polar ingredients such as tackifiers, plasticizers and waxes such that the water sensitivity of the thermoplastic component as a whole is sufficiently reduced such that the composition exhibits the desired rate of acquisition. Representative water soluble or water dispersible polymers that may be employed in this manner include water soluble polyamides such as those described in U.S. Pat. No. 3,882,090, incorporated herein by reference, amorphous water sensitive thermoplastic polymers such as polyvinyl alcohol (PVOH) available from Nippon Grohsei as Grohseran L-301 and Grohseran L-302, polyvinyl pyrrolidone (PVP) available from BASF and ISP, polyvinyl pyrrolidone/vinyl acetate copolymer (PVPNVA) available from ISP, polyetheroxazoline available from Dow under the tradename PEOX and from PCI Incorporated under the tradename Aquazol, polyvinyl methyl ether available from Amoco Chemical Co. under the tradename Amobond, linear polyesters, polyvinyl alcohol, polyacrylamide, water dispersible copolyesters (Eastman AQ).

The thermoplastic component of the composition of the present invention preferably further comprises at least one additional ingredient in an amount up to about 50 wt-%, and preferably from about 10 wt-% to about 40 wt-% with respect to the total composition. Preferred thermoplastic ingredients include those that are commonly employed in hot melt adhesive compositions including plasticizers, tackifiers, waxes, and additives such as antioxidants and pigments. In general, the type of thermoplastic ingredient(s) will be selected to insure sufficient compatibility of the thermoplastic component as a whole. In a preferred embodiment, the thermoplastic component of the composition of the present invention comprises at least one diluent having polar functionality. The diluent is preferably a plasticizer or wax having a molecular weight (Mw) of less than 3000 and preferably less than 2000. The diluent is preferably water insensitive, yet sufficiently polar to reduce the surface tension and/or contact angle of the thermoplastic composition relative to a comparative composition comprising the same ingredients in the absence of such ingredient. Polar diluents include plasticizers and waxes having at least one polar group per molecule. The polar group may be a terminal group or bonded to one or more units in the middle of the molecule. Polar groups include alcohol, ether, ester, epoxy, carboxylic acid, amine, amide, aldehyde, keton, oxime, sulphonic acid, and sulfonamide groups. It is surmised that the polar diluent may plasticize the SAP. Hence, combining the SAP with polar plasticizer alone may increase the absorption rate. However, in the absence of a polymer, plasticizer alone typically could not contribute a continuous thermoplastic phase to disperse the SAP within. Preferably, the diluent is employed at an amount ranging from about 5 wt-% to about 30-wt-% and more preferably in an amount ranging from about 10 wt-% to about 20 wt-% of the total composition.

Exemplary polar plasticizers include phthalate plasticizers such as dioctyl phthalate and butyl benzyl phthalate (e.g., Santicizer 160 from Monsanto); liquid polyesters such as Dynacol 720 from Huls and liquid polymeric plasticizer available from C. P. Hall; benzoate plasticizers such as 1,4-cyclohexane dimethanol dibenzoate (e.g., Benzoflez 352 from Velsicol), diethylene glycol/dipropylene glycol dibenzoate (e.g., Benzoflez 50 from Velsicol), and diethylene glycol dibenzoate where the mole fraction of hydroxyl groups which have been esterified ranges from 0.5 to 0.95 (e.g., Benzoflex 2-45 High Hydroxyl also from Velsicol); phosphite plasticizers such as t-butyl diphenyl phosphate (e.g., Santicizer 154 from Monsanto); liquid rosin derivatives having Ring and Ball softening points below about 60° C. such as methyl ester of hydrogenated rosin (e.g., Hercoyn D from Hercules); as well as vegetable and animal oils such as glycerol esters of fatty acids and polymerizable products thereof. Preferred plasticizers include esters of citric acid such as Citroflex® 2, A-2, 4, A-4, A-6, and B-6; butyl benzyl phthalate, toluene sulfonamide, benzoate plasticizers such as 1,4-cyclohexane dimethanol dibenzoate, diethylene glycol/ dipropylene glycol dibenzoate, and diethylene glycol dibenzoate where the mole fraction of hydroxyl groups which have been esterified ranges from 0.5 to 0.95.

Further, water soluble or water dispersible plasticizers may also be employed, provided the presence thereof does not impede the rate of absorption of the SAP. Suitable examples include polyethylene glycol with molecular weight below about 2000 and preferably less than 1000, derivatives of polyethylene glycol including Pycal 94, the phenyl ether of PEG available from ICI; ethoxylated bis phenol A (e.g., Macol 206 EM from PPG Industries) and dionyl phenol ethyloxylates (e.g., Surfonic DNP from Huntsman Chemical Corp.).

Exemplary polar waxes include 12-hydroxystearamide, N-(2-hydroxy ethyl 12-hydroxy stearamide (Paricin 220 and 285 from CasChem), stearamide (Kemamide S from Witco), glycerin monostearate, sorbitan monostearate, and 12-hydroxy stearic acid. Also useful in combination with the above are less polar waxes such as N,N'-ethylene-bis stearamide (Kemamide W-40 from Witco), hydrogenated castor oil (castor wax), oxidized synthetic waxes, and functionalized waxes such as oxidized polyethylene waxes (Petrolite E-1040).

Other useful plasticizers that may be employed include hydrocarbon oils, polybutene, liquid tackifying resins and liquid elastomers. Plasticizer oils are primarily hydrocarbon oils which are low in aromatic content and which are paraffinic or naphthenic in character. Plasticizer oils are preferably low in volatility, transparent and have as little color and odor as possible. The use of plasticizers in this invention also contemplates the use of olefin oligomers, low molecular weight polymers, vegetable oils and their derivatives and similar plasticizing liquids.

Waxes are usefully employed to reduce viscosity as well as increase the blocking resistance at concentrations ranging from about 2 wt-% to about 25 wt-% and preferably from about 10 wt-% to about 20 wt-%. Larger concentrations of waxes are typically avoided since waxes tend to bloom to the surface during cooling of the thermoplastic component creating a fluid impermeable barrier layer at the surface of the composition or encapsulating the SAP, thus hindering the ability of the SAP to absorb fluid. In addition to the preferred polar waxes, other useful waxes include paraffin waxes, microcrystalline waxes, Fischer-Tropsch, polyethylene and by-products of polyethylene.

As used herein, the term "tackifier" means any of the compositions described below that are useful to impart tack to the hot melt adhesive composition. ASTM D-1878-61T defines tack as "the property of a material which enables it to form a bond of measurable strength immediately on contact with another surface".

The composition of the invention may comprise up to about 50 wt-% of a tackifying resin. Tackifying resins are preferably employed at a concentration ranging from about 5 wt-% to about 40 wt-% and more preferably from about 10 wt-% to about 20 wt-% with respect to the total weight of the composition.

Tackifying resins comprise resins derived from renewable resources such as rosin derivatives including wood rosin, tall oil and gum rosin as well as rosin esters, natural and synthetic terpenes and derivatives of such. Aliphatic, aromatic or mixed aliphatic-aromatic petroleum based tackifiers are also useful in the invention. Representative examples of useful hydrocarbon resins include alpha-methyl styrene resins, branched and unbranched $C_5$ resins, $C_9$ resins and $C_{10}$ resins, as well as styrenic and hydrogenated modifications of such. Tackifying resins range from being a liquid at 37° C. to having a ring and ball softening point of about 135° C.

As is known in the art, various other components can be added to modify the tack, color, odor, etc., of the thermoplastic composition. Additives including antioxidants such as hindered phenolics (e.g., Irganox™ 1010, Irganox™ 1076), phosphites (e.g., Irgafos™ 168), antiblock additives, pigments and fillers, can also be included in the formulations.

Hydrophilic fillers are a preferred class of additives, which are useful to alter the surface properties and/or increase the rate of absorption. Hydrophilic fillers include calcium carbonate, hydroxyethyl cellulose, hydroxypropyl cellulose and starch or cellulose esters, particularly the acetates.

Surfactants are another preferred additive that reduces the surface tension and/or contact angle of the thermoplastic component. Surfactants are useful in amounts ranging from about 0.5 wt-% to about 25 wt-% and preferably from about 5 wt-% to about 15 wt-% with respect to the total weight of the thermoplastic component. Suitable surfactants include nonionic, anionic, and silicone surfactants. Exemplary nonionic surfactants are: Ethoxylates of (i) C sub 1-C sub 18, preferred C sub 8-C sub 9 alkyl or dialkyl phenols, such as those sold under the tradenames Macol DNP-10, available from PPG Industries, Gurnee, Ill., a 10 mole ethoxylate of dinonyl phenol, and Triton X-100, available from Union Carbide, a 10 mole ethoxylate of octyl phenol; (ii) alkyl C sub 8-C sub 60 mono-alcohols such as those sold under the tradenames Surfonic L-12-8, an 8 mole ethoxylate of dodecanol, available from Huntsman Chemical Co., and Unithox 480, a 38 mole ethoxylate crystalline surfactant available from Petrolite Specialty Polymers Group, Tulsa, Okla.; and (iii) propylene oxide polymers, such as those sold under the tradename Pluronic, which are ethylene oxide/ propylene oxide block copolymers having a Mn of 200 to 3000, available from BASF; and benzoates formed by partial condensation of benzoic acid with hydrophilic di or mono-ols having less than 1000 Mn, such as the product of condensing about three equivalents of benzoic acid with four equivalent of diethylene glycol, commercially available as XP 1010 from Velsicol Chemical. A preferred nonionic surfactant blend is Atmer 685, available from ICI Surfactants (Wilmington, Del.).

Suitable anionic surfactants are: C sub 8-C sub 60 alkyl ethoxylate sulfonates, (CH sub 3—(CH sub 2) sub 11–14— (O—CH sub 2 CH sub 2) sub 3—SO sub 3-Na sup+, such as, Avenel S30, available from PPG Industries; alkyl C sub 8-C sub 60 sulfonates, such as, Rhodapon UB (C sub 12 —SO sub 3 sup −Na sup+) available from Rhone Poulenc; and alkyl/aromatic sulfonates, such as those sold under the tradename Calsoft.

Suitable silicone surfactants are ethoxylates or propoxylates of polydimethyl siloxane, having a number average molecular weight of 500 to 10,000, preferably 600 to 6000, such as are sold under the tradenames Silwet L-77, L-7605, and L-7500 available from OSi Specialties, Danbury, Conn.; and product 193 from Dow Corning.

The preferred surfactants are those with lower molecular weights because these have increased compatibility in the adhesive formulations. The maximum acceptable molecular weight depends on the type of surfactant and the other ingredients in the adhesive formulation.

The thermoplastic component is characterized as having a Brookfield molten viscosity of less than about 30,000 cPs at 177° C., preferably less than about 20,000 cPs, more preferably less than about 10,000 cPs, and even more preferably less than about 5,000 cPs. This viscosity constraint does not necessarily have a lower limit. However, the majority of thermoplastic compositions contemplated for use generally have a viscosity of at least about 50 cPs at 100° C., typically at least about 100 cPs, and preferably at least about 200 cPs. The viscosity is not only critical to the application techniques intended for such composition, but is also critical to the efficiency of the SAP. The present applicants have surprisingly discovered that relatively low viscosity thermoplastic compositions constrain the swelling of the SAP particle to a much lesser extent and hence improve the absorption of the SAP with respect to a high viscosity based composition.

The thermoplastic composition of the present invention comprises at least one SAP polymer admixed with the thermoplastic component. The superabsorbent polymer is present in the composition in an amount ranging from about 5 wt-% to about 70 wt-%, preferably from about 35 wt-% to about 60 wt-%, more preferably ranging from about 40 wt-% to about 60 wt-%, and most preferably from about 50 wt-% to about 60 wt-%. The Applicants have found that by employing SAP at concentration greater than 30 wt-%, particularly in combination with small particle size SAP, a matrix of SAP is formed with the thermoplastic component. The applicants surmise that the formation of this SAP matrix is essential to the absorption rate of the SAP being unaffected by the presence of the thermoplastic component.

Superabsorbent polymers (SAP), also referred to as water-insoluble absorbent hydrogel-forming polymers (WAHPs) "hydrogel-forming" polymers, and "hydrocolloids" are known and include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, WABPs useful in the present invention have a plurality of anionic, functional groups, such as sulfonic acid, and more typically carboxy, groups. Examples of polymers suitable for use herein include those which are prepared from polymerizable, unsaturated, acid-containing monomers. Such monomers include the olefinically unsaturated acids and anhydrides that contain at least one carbon to carbon olefinic double bond. More specifically, these monomers can be selected from olefinically unsaturated carboxylic acids and acid anhydrides, olefinically unsaturated sulfonic acids and mixtures thereof.

Some non-acid monomers can also be included, preferably in minor amounts, in preparing the SAPs herein. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups and aryl groups (e.g., phenyl groups, such as those derived from styrene monomer). These non-acid monomers are well-known materials and are described in greater detail, for example, in U.S. Pat. No. 4,076,663 (Masuda et. al), issued Feb. 28, 1978, and in U.S. Pat. No. 4,062,817 (Westerman), issued Dec. 13, 1977.

Olefinically unsaturated carboxylic acid and carboxylic acid anhydride monomers include the acrylic acids typified by acrylic acid itself, methacrylic acid, ethacrylic acid, chloroacrylic acid, -cyanoacrylic acid, -methylacrylic acid (crotonic acid), -phenylacrylic acid, -acrytoxypropionic acid, sorbic acid, -chlorosorbic acid, angelic acid, cinnamic acid, p-chlorocinnamic acid, -stearylacrylic acid, itaconic acid, citraconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy 3-methacryloxypropyl sulfonic acid and 2-acrylamide-2-methylpropane sulfonic acid.

Other SAPs for use in the present invention contain carboxy groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 4,076,663 (Masuda et. al), issued Feb. 28, 1978, U.S. Pat. No. 4,093,776 (Aoki et. al), issued Jun. 6, 1978, U.S. Pat. No. 4,666,983(Tsubakimoto et. al), issued May 19, 1987, and U.S. Pat. No. 4,734,478 (Tsubakimoto et. al), issued Mar. 29, 1988.

Polymer materials used in making the SAPs are slightly network crosslinked polymers of partially neutralized polyacrylic acids and starch derivatives thereof. More preferably still, the SAPs comprise from about 50% to about 95%, more preferably about 75%, neutralized, slightly network crosslinked, polyacrylic acid (i.e., poly (sodium acrylate/acrylic acid)). Network crosslinking renders the polymer substantially water-insoluble and, in part, determines the absorptive capacity and extractable polymer content characteristics of the SAPs. Processes for network crosslinking these polymers and typical network crosslinking agents are described in greater detail in U.S. Pat. No. 4,076,663 (Masuda et. al), issued Feb. 28, 1978.

While the SAP is preferably of one type (i.e., homogeneous), mixtures of polymers can also be used in the present invention. For example, mixtures of starch-acrylic acid graft copolymers and slightly network crosslinked polymers of partially neutralized polyacrylic acid can be used in the present invention.

The absorbent gelling particles used in the present invention can have a size, shape and/or morphology varying over a wide range. The absorbent gelling particles may have a large ratio of greatest dimension to smallest dimension (e.g., granules, flakes, pulveruients, interparticle aggregates, interparticle crosslinked aggregates, and the like) and can be in the form of fibers, foams and the like.

Particle size is defined as the dimension determined by sieve size analysis. Thus, for example, a particle that is retained on a U.S.A. Standard Testing Sieve with 710 micron openings (e.g., No. 25 U.S. Series Alternate Sieve Designation) is considered to have a size greater than 710 microns; a particle that passes through a sieve with 710 micron openings and is retained on a sieve with 500 micron openings (e.g., No. 35 U.S. Series Afternate Sieve Designation) is considered to have a particle size between 500 and 710 microns; and a particle that passes through a sieve with 500 micron openings is considered to have a size less than 500.

For particles of SAPs employed in the present invention, the particle size ranges from about 10 to about 1000 microns. Smaller particle sizes, particularly at concentrations greater than 30 wt-%, and preferably about 40 wt-%, have been found to be particularly useful for creating a SAP matrix within the thermoplastic component. Minimal particle size is also advantageous to obtain homogeneous mixing as well as reduce the abrasion and nozzle clogging problems associated with processing relatively large particles using hot melt adhesive application equipment. For these reasons the particle size of the SAP is preferably less than about 500 microns, more preferably less than about 300 microns, and more preferably less than about 200 microns. However, larger particle size may also be employed particularly in applications in which the SAP particle is equal to or larger than the thickness of the thermoplastic component or when an extruder is employed to mix and/or apply the composition.

The composition of the present invention is preferably made by first preparing the thermoplastic component by melting and blending all the thermoplastic ingredients and then adding the SAP to the molten thermoplastic component. The SAP containing thermoplastic composition may be pelletized, pillowed, or cast into molds or drums, etc., for subsequent remelting and application. Alternatively, all the ingredients may be fed simultaneously at the appropriate rates into an extruder. In the case of extruders, the compounding and application of the SAP containing composition may be achieved in a single process.

In the case of foaming, it is preferred to first coat the SAP particles with a chemical blowing agent. The coated SAP particle is admixed with the thermoplastic component at a temperature below the activation temperature of the chemical blowing agent to prevent premature unintended foaming. The composition is then formed into a film or coated onto a substrate at a temperature or condition sufficient to activate the chemical blowing agent. The chemical blowing agent is surmised to create a gaseous cavity or void with the thermoplastic component with the SAP particle positioned within the void. Preferably, a sufficient amount of coated SAP is employed such that an open cell foam structure is created.

In another embodiment the SAP particles may be coated with the thermoplastic component in particulate form. The coated SAP particle may then be positioned within an article or on a substrate and then heat activated to adhere the SAP particle in place.

The coating of solid particles is done in a number of ways. Both spray drying and prilling are inexpensive methods for coating of particles. In both these processes the particle to be coated is added to the melt or solution and during atomization the coating is done. Another suitable method called Magnetically Assisted Impact Coating (MAIC), available by Aveka Inc. (Woodbury, Minn.), coats particle onto particle by means of a peening process. By adding a small coating particle onto a large particle core into an assembly of small oscillating magnets, the small particles are readily coated onto the core particles. A preferred method is a two step process of coating the SAP particle with a binder and then contacting the binder coated particle with a powder as described in U.S. Pat. No. 5,688,449 issued Nov. 18, 1997, incorporated herein by reference.

The viscosity of the mixture of thermoplastic component and SAP is less than about 200,000 cPs, preferably less than about 100,000, more preferably less than 50,000 at 350° F. (177° C.), and most preferably exhibits the same molten viscosity properties as previously described for the thermoplastic component alone.

The thermoplastic composition of the present invention gels at a rate equal to or faster than that of the superabsorbent polymer alone. Preferably, the composition gels in less than 3 hours, preferably in less than 2 hours, more preferably in less than 1 hour, even more preferably in less than 30 minutes, and most preferably in less than about 15 minutes. Further, for small particle size SAP, the total absorption capacity of the inventive composition is equal to or greater than that of the superabsorbent polymer alone.

The composition of the present invention may be applied by any hot melt application technique such as slot coating, spiral spraying, screen printing, foaming, engraved roller or meltblown adhesive application techniques. When applied in this manner, the inventive thermoplastic composition may be present as a coating, fiber, nonwoven web, or film layer on at least one substrate or as a portion of an article. Preferably, to improve the rate of absorption of the SAP, the application conditions are chosen to maximize the surface areas of the composition. The composition of the present invention may also be formed into a film layer. If a continuous film layer is desired, it is preferred to use a non-contact slot coating application technique described in U.S. Pat. No. 5,827,252 issued Oct. 27, 1998, incorporated herein by reference.

The SAP containing thermoplastic composition of the present invention is useful for a variety of end-uses, particularly those which employ superabsorbent polymers such as disposable absorbent articles such as disposable diapers, feminine napkins and medical dressings as well as moisture barriers for optical cable applications and a variety of agricultural applications targeted at increasing humectancy. The inventive composition has further utility in packaging application for food and drugs for absorbing moisture and fluid, for building materials for preventing condensation and waterproofing. Accordingly, the thermoplastic composition may be applied to a variety of substrates using any suitable method, particularly the hot melt adhesive application techniques described above. Substrates in which SAP is commonly applied to includes various film materials such as those employed as diaper backsheets and tape backings, absorbents such as wood pulp, paper, tissues and towels, nonwovens, and various cable components such as sheathing and jacketing materials.

The invention is further illustrated by the following non-limiting examples. All composition exemplified are expressed in wt-% unless noted otherwise.

EXAMPLE

Test Methods
1. Melt Viscosity is determined in accordance with the following procedure using a Brookfield Laboratories DVII+Viscometer in disposable aluminum sample chambers. The spindle used is a SC-27 hot-melt spindle, suitable for measuring viscosities in the range of from 10 to 100,000 centipoise. The sample is placed in the chamber, which is in turn inserted into a Brookfield Thermosel and locked into place. The sample chamber has a notch on the bottom that fits the bottom of the Brookfield Thermosel to ensure that the chamber is not allowed to turn when the spindle is inserted and spinning. The sample is heated to the desired temperature, with additional sample being added until the melted sample is about 1 inch (2.5 cm) below the top of the sample chamber. The viscometer apparatus is lowered and the spindle submerged into the sample chamber. Lowering is continued until brackets on the viscometer align on the Thermosel. The viscometer is turned on, and set to a shear rate which leads to a torque reading in the range of 30 to 60 percent. Readings are taken every minute for about 15 minutes, or until the values stabilize, which final reading is recorded.
2. Total Absorption is determined by drawing-down a molten film or heat-pressing the SAP comprising thermoplastic composition into a film. The film is then cut into a 1 inch (2.54 cm) square and weighed. The total amount of SAP in the film is calculated on the basis of the concentration of the SAP within the composition. The sample is then placed in a 25 ml cup and 10 mls of water is poured on top of the film. After 3 hours, the unabsorbed water is filtered off and weighed. The total amount of water absorbed is reported as well as the amount of water absorbed per gram of SAP (total absorbed/total SAP).
3. Rate of Absorption is determined by drawing-down a molten film or heat-pressing the SAP comprising thermoplastic composition into a film. The film is then cut into a 1 inch (2.54 cm) square and weighed. The total amount of SAP in the film is calculated on the basis of the concentration of the SAP within the composition. The sample is then placed in a 25 ml cup and 10 mls of water is poured on top of the film. A stopwatch is started and the time it takes for gelation to occur reported.
4. Melt Index is reported in accordance with ASTM D-1238, condition 190° C./2.16 kg (also known as "Condition E").

DESCRIPTION OF INGREDIENTS EMPLOYED IN THE EXAMPLES

| Tradename | Generic Description, Supplier (Location) |
|---|---|
| Thermoplastic Polymer | |
| Affinity EG 8200 | 5 MI, .870 g/cm$^3$ substantially linear ethylene/1-octene interpolymer, Dow (Freeport, TX) |
| Affinity EG 8100 | 1 MI, .870 g/cm$^3$ substantially linear ethylene/1-octene interpolymer, Dow (Freeport, TX) |
| Eastman Copolyester 14766 | biodegradable copolyester, Eastman (Kingsport, TN) |
| Eco PLA | polylactide resin, Cargill (Minneapolis, MN) |
| EVA 25-400 | 25% vinyl-acetate, 400 MI EVA |
| EVA 28-400 | 28% vinyl-acetate, 400 MI EVA |
| EVA 28-05 | 28% vinyl-acetate, 5 MI EVA |
| EVA 28-800 | 28% vinyl-acetate, 800 MI EVA |
| EVA 28-2500 | 28% vinyl-acetate, 2500 MI EVA |
| EVA 33-44 | 33% vinyl-acetate, 44 MI EVA |
| EVA 33-400 | 33% vinyl-acetate, 400 MI EVA |
| HL-6526 | polyamide polymer, (H. B. Fuller Company, St. Paul, MN) |
| HL-6582 | polyamide polymer, (H. B. Fuller Company, St. Paul, MN) |
| HM-1580 | polyamide polymer, (H. B. Fuller Company, St. Paul, MN) |
| HL-6594 | polyamide polymer, (H. B. Fuller Company, St. Paul, MN) |
| HL-6108 | polyamide polymer, (H. B. Fuller Company, St. Paul, MN) |
| Kraton D-1117 | 40% diblock, 17% styrene, 106 MI, styrene-isoprene-styrene block copolymer (Shell) |
| Kraton G-1657 | 35% diblock, 13% styrene, 370$^{11}$ solution viscosity styrene-ethylene/butylene-styrene block copolymer (Shell) |
| Plasticizers | |
| Benzoflex 50 | dipropylene-diethylene glycol dibenzoate, Velsicol (Rosemont, IL) |
| Benzoflex 9-88 | dipropylene glycol dibenzoate, Velsicol (Rosemont, IL) |
| Citroflex A4 special | citrate ester from citric acid, Morflex Inc. (Greensboro, NC) |
| Epolene C-3 | polyethylene wax, Eastman Chemical Co. (Kingsport, TN) |
| Epolene C-16 | polyethylene wax, Eastman Chemical Co. (Kingsport, TN) |
| Microwax 180 | polyethylene wax |
| Paraflint H4 | Fischer-Tropsch wax, Moore & Munger (Shelton, CT) |
| Paraffin 155 | 155° melt point paraffin wax |
| Penznap N-500 | 500 viscosity naphthenic oil |
| Santicizer 160 | 1,2 benzene dicarboxylic acid, butyl phenylmethylester, Solution Inc. (St. Louis, Missouri) |
| Uniplex 214 | N-butyl benzene sulfonamide, Unitex (Houston, TX) |
| Tackifiers | |
| Escorez 5400 | 100° C. hydrogenated dicyclopentadiene resin (Exxon, Houston, TX) |
| Foral AX | hydrogenated rosin, Hercules (Wilmington, DE) |
| Nirez V-2040 | 118° C. terpene phenolic based resin (Arizona, Panama City, FL |
| Zonester 100 | 94° C. rosin based resin (Arizona, Panama City, FL |
| Additives | |
| Surfactant JL80-X | alcohol ethoxylate surfactant, Huntsman (Houston, TX) |
| Irganox 1010 | hindered phenol antioxidant, Ciba Geigy (Hawthorne, NY) |
| Irganox 1076 | hindered phenol antioxidant Ciba Geigy (Hawthorne, NY) |
| Superabsorbent Polymers | |
| Aquapearl 1250H | sodium polyacrylate, Mitsubishi Chemical Co. (Tokyo, JP) |
| Cabloc AP-80HS | lightly crosslinked sodium polyacrylate, Stockhausen (Greensboro, NC) |

-continued

| Tradename | Generic Description, Supplier (Location) |
|---|---|
| Favor 800 | 2-propenoic acid polymers with hydroxyl ethenol homopolymer, Stockhausen (Greensboro, NC) |

Due to differences in base chemistry as well as particle size, the gel time of commercially available grades of SAP varies widely. The particle size distribution and gel time of the SAP employed in the examples can be characterized as follows in Table I. "D(10%), D(50%), and D(90%)" refers to the percentage of particle below X microns.

Hence, in the case of ASAP 2000, 10% of the particles have a particle size of less than 12.5 microns, 50% of the particles have a particle size of less than 62.9 microns, and 90% of the particles have a particle size of less than 561.7 microns.

TABLE I

| Tradename of SAP | D(10%) | D(50%) | D(90%) | Weight (g) | Gel Time |
|---|---|---|---|---|---|
| Cabloc 80HS | 12.5 | 62.9 | 118 | 0.30 | 9 minutes |
| Cabloc 80 HS | | | | 0.15 | 25 minutes |
| ASAP 2000 (Standard) | 208.8 | 395.5 | 561.7 | 0.31 | 1 Min. 20 Sec |
| Femdry 31 | | | | 0.31 | 20 Sec |

Since particle size distribution SAP tends to be very disperse, Favor 800 was separated into fractions with Vortisiv RBF 8 (MM Industries, Salem, Ohio) metallic sieve and separation equipment. The resulting three portions had particles >425 microns, particles 180–425 microns, and particles <180 microns.

Examples 1–5 of Table II employ a thermoplastic adhesive composition comprising 80 g of Uniplex 214, 304 g of EVA 28-800, 36 g of Surfactant JL-80X and 4 g of Irganox 1076 in combination with Favor 800 super absorbent polymer at the indicated concentration and particle size. By comparing Example 1 to Example 4, the effect of increasing SAP concentration as a function of absorption rate is exemplified. Example 1 and 4 both contain the same particle size SAP, >425 microns. However, the composition comprising 40 wt-% SAP gelled 2.5 times faster than the composition employing only 30 wt-%. Examples 2 –4 employ 40 wt-% of the same SAP differing only with respect to the particle size of the SAP. These examples demonstrate that the fastest rate of gelation is achieved with the smallest particle size. The sample employing <180 micron particle size SAP absorbed the fluid 4 times faster than the sample employing the 180–425 micron SAP.

TABLE II

| | Rate of Absorption |
|---|---|
| Example 1 Adhesive + 30 wt-% > 425 microns | 1680 seconds |
| Example 2 Adhesive + 40 wt-% 180–425 microns | 900 seconds |
| Example 3 Adhesive + 40 wt-% < 180 microns | 160 seconds |
| Example 4 Adhesive + 40 wt-% > 425 microns | 660 seconds |

TABLE II-continued

| | Rate of Absorption |
|---|---|
| Example 5 Adhesive + 40 wt-% ASAP 2000 | >18000 seconds |
| Example 6 Adhesive + 40 wt-% AP80HS | 840 seconds |

μm = micron

Tables III to XI exemplify compositions of the present invention employing a variety of water insensitive thermoplastic polymers. Example 10 of Table III and Examples 69 and 70 of Table XI employ a substantially linear ethylene interpolymer. Examples 9 and 12–14 of Table III and IV as well as Tables V to IX in their entirety employ an ethylene interpolymer comprising a polar comonomer. Examples 7, 8 and 11 of Table III and Example 71 of Table XI depict compositions wherein the thermoplastic component is based on a biodegradable thermoplastic material.

Example 7 was found to absorb 10 mls of water in 100 seconds, whereas Example 8 was found to exhibit a slower absorption rate of 190 seconds. Additionally, Example 8 was noted to be very flexible due to the incorporation of the block copolymer.

Table IV exemplifies the rate of absorption for various inventive compositions of the present invention as well as commercially available comparative examples.

According to infrared analysis as well as solvent extraction and centrifugation analytical techniques, Comparative A is believed to comprise about 33.8 wt-% of a 33% vinyl acetate/44 MI EVA, about 47.3 wt-% high molecular weight (about 10,000) polyethylene glycol, and about 18.9 wt-% sodium salt of polyacrylic acid, whereas Comparative B is believed to comprise about 42.6 wt-% of a 28% vinyl acetate/400 MI EVA, about 26.8 wt-% polyoxyethylene stearate, about 29.5 wt-% polyacrylic acid, and about 1.1 wt-% wax. Comparative C represents a composition made in accordance with Doi et al., U.S. Pat. No. 4,977,211. Specifically, 45 wt-% of LV-780 ethylene-vinyl acetate was combined with 15 wt-% of USR E P02P polyethylene and 40 wt-% of Aquapearl 1250H. The relatively slow absorption rate is surmised to be attributed to the high cohesive strength of the thermoplastic component.

The EVA content of the inventive EVA based compositions of Tables V and VI varies from 20 wt-% to about 70 wt-%. The rate of gelation increases dramatically at SAP concentrations greater than 30 wt-%. Further, by comparing Examples 15 to 16 of Table V, it is apparent that the addition of plasticizer tends to further increase the rate of acquisition. The Applicants surmise that this effect is attributed to the increased polarity contributed by the plasticizer and/or a further reduction in cohesive strength of the thermoplastic component as a result of the dilution.

A 0.15 g sample of the superabsorbent polymer Cabloc 80HS alone, in the absence of being combined with a thermoplastic composition in Table I, took 25 minutes to gel. However, Examples 13–15, all containing about the same amount of SAP gel significantly faster, ranging in rate of gelation from about 3 minutes to about 13 minutes. The Applicants surmise that the thermoplastic component separates the individual SAP particles from each other. Accordingly, each SAP particle can absorb fluid and swell independently, essentially unaffected by the surrounding SAP particles. Hence, gel blocking, the phenomena wherein the gelled SAP particles create a barrier and prevent the migration of fluid to the ungelled SAP particles, is reduced, increasing the rate of gelation.

Table VII demonstrates the effect of polar comonomer content and melt index on the rate of gelation. As exemplified by Examples 27, 28 and 30 as the comonomer content increases from 25 wt-% to 28 wt-% to 33 wt-%, the rate of gelation decreases from 24 hours, to about 30 minutes to about 15 minutes. Hence, polar comonomer contents of greater than 25 wt-% are preferred, and greater than 28 wt-% most preferred. Further, as exemplified by Examples 29 and 31–34, as the melt index increases, the gel rate decreases. However, regardless of the melt index of the ethylene interpolymers, all these examples exhibit a substantially faster gel rate than Comparative Examples A to C. The Applicants surmise that the relatively low concentration of SAP causes the reduced gel rate of the comparative examples in view of Examples 21 to 24 of Table IV depicting the gel rate of high SAP containing formulations in comparison to low SAP containing formulations.

as the thermoplastic component. Employing polyamides is advantageous to increase the heat resistance as well as increase the concentration of SAP. Example 68 employs 70 wt-% SAP, yet remains flexible.

Table XI depicts compositions of the present invention wherein the thermoplastic component contributes elastomeric properties. Examples 69 and 70 employ a substantially linear ethylene/alpha-olefin interpolymer, whereas examples 71 and 72 employ saturated block copolymers. Specifically, Preblend A contains 7 wt-% Kraton G-1651, 17 wt-% Kraton G-1650, 75.25 wt-% Kaydol mineral oil and 0.25 wt-% Irganox 1010. These compositions can advantageously be sprayed to form a flexible web or slot coated to form a flexible film. The film expands several folds in dimension when exposed to water depending on the concentration of SAP. Surprisingly, the film maintains its integrity after swelling.

TABLE III

| Ingredient Tradename | Ex. 7 | Ex. 8 | Ex. 9 | Ex. 10 | Ex. 11 | Ex. 12 | Ex. 13 | Ex. 14 |
|---|---|---|---|---|---|---|---|---|
| Cabloc AP-80HS | 50 | 50.0 | 49.8 | 50 | 54.90 | 50.10 | | 40 |
| Aquapearl 1250H | | | | | | | | |
| Irganox 1076 | | | 0.4 | | | | 0.5* | 0.5* |
| Eastman Copolyester 14766 | 30 | 31.5 | | | | | | |
| Kraton D-1117 | | 8.0 | | | | | | |
| Santicizer 160 | 20 | 10.5 | | | | 13.63 | | |
| Benzoflex 50 | | | 9.10 | | | | | |
| Benzoflex 9-88 | | | | 22.72 | | | | |
| Citroflex A4 | | | | | 10.15 | | 18 | 18 |
| EVA 28-400 | | | 36.2 | | | | | |
| EVA 28-800 | | | | | | 36.28 | 41.5 | 41.5 |
| Eco PLA | | | | | 34.94 | | | |
| Surfactant JL80-X | | | 4.50 | | | | | |
| Affinity EG 8200 | | | | 27.27 | | | | |
| Total Parts | 100.0 | 100.0 | 99.96 | 99.99 | 99.99 | 100 | 60 | 100.01 |

*Irganox 1010

Table VIII exemplifies compositions of the present invention comprising wax. In comparison to Example 33, a portion of the plasticizer may be replaced with wax resulting in similar gel rates. The use of Paraffin 155 and Microwax 180 results in faster gel rates. However, as depicted by Example 44, this accelerated rate can only be achieved by employing a combination of polar plasticizer and wax, since wax alone results in a slower gel rate.

Examples 45 to 49 of Table IX exemplify compositions of the present invention comprising tackifier. In comparison to Example 33, by replacing a portion of the plasticizer with tackifier the composition exhibits comparable gel rates. Examples 50 to 56 of Table IX as well as Examples 9 and 12 of Tables III exemplify compositions of the present invention comprising surfactant. Example 37 also contains 4.5 wt-% of Surfactant JL80-X. As in the case of tackifiers, a portion of the polar plasticizer may be replaced with surfactant resulting in comparable and in some instances accelerated gel rates.

Table X exemplifies compositions comprising water insensitive polyamides in combination with polar plasticizer

TABLE IV

| Example | Dry Sample Wt. | Time Elapsed until Gelation | Viscosity of Thermoplastic Component @ 350° F. (177° C.) CPs |
|---|---|---|---|
| Ex. 9 | 0.3716 | 2' 38" | |
| Ex. 11 | 0.2808 | 3' 30" | 870 |
| Ex. 12 | 0.2837 | 4' 0" | 3065 |
| Ex. 10 | 0.4500 | 15' 0" | |
| Ex. 13 | | 13" | 6740 |
| Ex. 14 | | 12" | 11,900 |
| Comparative A | 0.3218 | >3 hours | |
| Comparative B | 0.3300 | >3 hours | |
| Comparative C | | 300 minutes | |

TABLE V

| Example | SAP Cabloc 80 HS (wt-%) | EVA 28-800 (wt-%) | Santicizer 160 (wt-%) | TOTAL (%) | Film Thickness Mils | Film Weight* grams | Gel Time minutes |
|---|---|---|---|---|---|---|---|
| Ex. 15 | 50.0 | 30.0 | 20.0 | 100.0 | 14 | 0.268 | 3 |
| Ex. 16 | 50.0 | 37.5 | 12.5 | 100.0 | 15 | 0.263 | 5 |
| Ex. 17 | 40.0 | 45.0 | 15.0 | 100.0 | 14 | 0.264 | 13 |
| Ex. 18 | 30.0 | 52.5 | 17.5 | 100.0 | 16 | 0.227 | 480 |
| Ex. 19 | 20.0 | 60.0 | 20.0 | 100.0 | 17 | 0.242 | 1440 |
| Ex. 20 | 10.0 | 67.5 | 22.5 | 100.0 | 18 | 0.264 | >4320 |

*Since the composition comprises 50 wt-% SAP, the weight of SAP = "Film Weight"/2

TABLE VI

| Example | EVA 33-400 (wt-%) | EVA 33-44 (wt-%) | Benzoflex 50 (wt-%) | Santicizer 160 (wt-%) | Cabloc 80-HS (wt-%) | Film Thickness mils | Film Weight grams | Gel Time |
|---|---|---|---|---|---|---|---|---|
| Ex. 21 | 11.16 | 18.84 |  | 20.00 | 50.00 | 9.0 | 0.1762 | 7 min 25 sec |
| Ex. 22 | 17.85 | 30.15 |  | 32.00 | 20.00 | 10.6 | 0.1931 | over 6 hours |
| Ex. 23 | 11.16 | 18.84 | 20.00 |  | 50.00 | 11.5 | 0.19999 | 8 min & 40 sec |
| Ex. 24 | 17.85 | 30.15 | 32.00 |  | 20.00 | 11.8 | 0.1800 | over 6 hours |

TABLE VII

| Example # | 25 | 26 | 27 | 28 | 29 | 30 | 31 | 32 | 33 | 34 |
|---|---|---|---|---|---|---|---|---|---|---|
| Ingredient |  |  |  |  |  |  |  |  |  |  |
| Cabloc 80 HS | 50 | 50 | 50 | 50 | 50 | 50 | 50 | 50 | 50 | 50 |
| EVA 25-400 |  |  | 50 |  |  |  |  |  |  |  |
| EVA 28-400 |  |  |  |  |  |  | 50 |  | 35 |  |
| EVA 33-400 |  |  |  | 50 |  |  |  |  |  |  |
| EVA 28-800 | 36.3 | 34.5 |  |  |  |  |  | 30 |  |  |
| EVA 28-2500 |  |  |  |  |  |  |  | 50 |  | 30 |
| EVA 28-03 |  |  |  |  | 18.2 |  |  |  |  |  |
| Citroflex A-4 |  | 15 |  |  | 31.8 |  |  | 20 | 15 | 20 |
| Uniplex 214 | 13.2 |  |  |  |  |  |  |  |  |  |
| Irganox 1010 | 0.5 | 0.5 |  |  |  |  |  |  |  |  |
| Tests results and observations |  |  |  |  |  |  |  |  |  |  |
| Film appearance | Flexible bleed | Flexible | Strong flexible | Strong flexible | Flexible | Strong flexible | Strong flexible | Flexible | Good flexible film | Flexible |
| Avg. Gel time (1" × 1" (2.54 cm × 2.54 cm) about 0.3 g film in 10 ml water) | 5 min | 6 min | over 24 hours | 15 min. 30 sec. | Expands while gelling (13 min) | 36 min. 15 sec. | 6 min 15 sec | 4 min. 33 sec. | 6 min 50 sec | 1 min 40 sec |

TABLE VIII

| Example No. | 35 | 36 | 37 | 38 | 39 | 40 | 41 | 42 | 43 | 44 |
|---|---|---|---|---|---|---|---|---|---|---|
| Cabloc 80 HS | 50.0 | 50.0 | 50.0 | 50.0 | 50.0 | 50.0 | 50.0 | 50.0 | 50.0 | 50.0 |
| EVA 28-800 | 29.7 | 29.7 | 29.7 | 29.7 | 29.7 | 29.7 | 24.0 | 24.0 | 24.0 | 34.5 |
| AC-400 | 8.0 |  |  |  |  |  |  |  |  |  |
| Paraffin 155F |  | 8.0 |  |  |  |  | 16.0 |  |  |  |
| Microwax 180F |  |  | 8.0 |  |  |  |  | 16.0 |  | 15.0 |
| Epolene C-3 |  |  |  | 8.0 |  |  |  |  | 16.0 |  |
| Epolene C-16 |  |  |  |  | 8.0 |  |  |  |  |  |
| Paraflint H4 |  |  |  |  |  | 8.0 |  |  |  |  |
| Citroflex A-4 | 12.0 | 12.0 | 12.0 | 12.0 | 12.0 | 12.0 | 9.7 | 9.7 | 9.7 |  |
| Irganox 1010 | 0.3 | 0.3 | 0.3 | 0.3 | 0.3 | 0.3 | 0.3 | 0.3 | 0.3 | 0.5 |

TABLE VIII-continued

| Example No. | 35 | 36 | 37 | 38 | 39 | 40 | 41 | 42 | 43 | 44 |
|---|---|---|---|---|---|---|---|---|---|---|
| Property Tests results and Gel time (fluid absorption) | | | | | | | | | | |
| Film appearance | less flexible | less flexible | flexible | flexible | flexible | slightly flexible | slightly brittle | slightly brittle | slightly brittle | slightly brittle |
| Avg. Gel time (1" × 1" (2.54 cm × 2.54 cm) about 0.3 g film in 10 ml water) | 5 minutes | 3 minutes 15 seconds | 3 minutes 45 seconds | 6 minutes 20 Seconds | 6 minutes 20 seconds | 7 minutes 45 seconds | 2 minutes 48 seconds | 2 minutes 30 seconds | 2 minutes 52 seconds | 9 minutes 45 seconds |

TABLE IX

| Example No. | 45 | 46 | 47 | 48 | 49 | 50 | 51 | 52 | 53 | 54 | 55 | 56 |
|---|---|---|---|---|---|---|---|---|---|---|---|---|
| Ingredient | | | | | | | | | | | | |
| Cabloc 80 HS | 50.0 | 50.0 | 50.0 | 50.0 | 50.0 | 48.9 | 47.0 | 47.0 | 47.0 | 40.0 | 40.0 | 40.0 |
| EVA 28-800 | 29.7 | 29.7 | 29.7 | 29.7 | 24.0 | 33.6 | 32.4 | 32.4 | 32.4 | 40.0 | 40.0 | 41.5 |
| CAB-O-SIL-m5 | | | | | | 2.5 | | | | | | |
| Emerest 2400 | | | | | | | | 6.0 | | | | |
| Pluronic F-38 | | | | | | | | | 6.0 | | 5.0 | |
| Pluronic F0108 | | | | | | | | | | 6.0 | | 5.0 |
| Zonester 100 | | | | 8.0 | 16.0 | | | | | | | |
| Nirez V-2040 | 8.0 | | | | | | | | | | | |
| Escorez 5400 | | 8.0 | | | | | | | | | | |
| Foral AX | | | 8.0 | | | | | | | | | |
| Citroflex A-4 | 12.0 | 12.0 | 12.0 | 12.0 | 9.7 | 14.5 | 14.1 | 14.1 | 14.1 | 15.0 | 15.0 | 18.0 |
| Irganox 1010 | 0.3 | 0.3 | 0.3 | 0.3 | 0.3 | 0.5 | 0.5 | 0.5 | 0.5 | | | 0.5 |
| Property Tests results and Gel time (fluid absorption) | | | | | | | | | | | | |
| Film appearance | flexible | flexible | flexible | sets slow, flexible | sets slow and flexible | flexible | flexible | flexible | flexible | flexible | flexible | flexible, sprayable |
| Avg. Gel time (1" × 1" (2.54 cm × 2.54 cm) about 0.3 g film in 10 ml water) | 5 minutes 40 seconds | 6 minutes 30 seconds | 7 minutes 25 seconds | 5 minutes 15 seconds | 5 minutes 20 seconds | 6 minutes 30 seconds | 6 minutes 40 seconds | 6 minutes 35 seconds | 5 minutes 5 seconds | 4 minutes 35 seconds | 4 minutes 50 seconds | |

TABLE X

| Example # | 57 | 58 | 59 | 60 | 61 | 62 | 63 | 64 | 65 | 66 | 67 | 68 |
|---|---|---|---|---|---|---|---|---|---|---|---|---|
| Ingredient | | | | | | | | | | | | |
| HL-6526 | 42.0 | 32.0 | | | | | | 8.0 | 6.4 | | 40 | 24.0 |
| HL-6582x | | | 42.0 | 32.0 | | 20.0 | | 32.0 | 25.6 | | | |
| HM 1580 | | | | | 40.0 | 20.0 | | | | | | |
| HL 6594 | | | | | | | 40.0 | | | | | |
| HL 6108 | | | | | | | | | | 40.0 | | |
| Benzoflex 9-88 | | | | | | | 10.0 | | | | | |
| Uniplex 214 | 8.0 | 8.0 | 8.0 | 8.0 | 10.0 | 10.0 | | 10.0 | 8.0 | 10.0 | 10 | 6.0 |
| Cabloc 80 HS | 50.0 | 60.0 | 50.0 | 60.0 | 50.0 | 50.0 | 50.0 | 50.0 | 60.0 | 50.0 | 50 | 70.0 |
| Irganox 1010 | | | | | | | | | | | | |
| Test results and observations | | | | | | | | | | | | |
| Film appearance | slow setting flexible | slow setting flexible | brittle | very brittle | flexible | flexible | slow setting tacky | brittle | brittle | flexible slow setting and | flexible | flexible |

TABLE X-continued

| Example # | 57 | 58 | 59 | 60 | 61 | 62 | 63 | 64 | 65 | 66 | 67 | 68 |
|---|---|---|---|---|---|---|---|---|---|---|---|---|
| Avg. Gel time (1" × 1" (2.54 cm × 2.54 cm) about 0.3 g film in 10 ml water) | 7 min. 5 sec. | 5 min. | 4 min. 20 sec. | 4 minutes | 7 min | 4 min. 30 sec. | 2 min 40 sec. | 2 min. 20 sec. | 2 min | tacky 2 min. 20 sec. | 12 minutes 20 seconds | |

TABLE XI

| Example No. | 69 | 70 | 71 | 72 |
|---|---|---|---|---|
| Ingredient | | | | |
| Cabloc 80 HS | 50 | 50 | 50 | 50 |
| Irganox 1010 | | | | |
| Benzoflex 8-88 | 12 | 15 | | 10 |
| Ciroflex A-4 | | | | |
| Penznap N500 oil | 26 | 20 | | |
| Kraton G1657 | | 5 | | |
| Preblend A | | | 50 | 40 |
| Copolyester 14766 | | | | |
| EG 8100 | 12 | 10 | | |
| Property test results | | | | |
| Film | very elastic, flexible, expanded in fluid bleed. | didn't bleed, flexible, elastic, expandable | flexible | flexible |
| Gel time | over 30 min. | 7 minutes | Expanded in one hr. | 7 minutes |

What is claimed is:

1. A thermoplastic composition comprising a thermoplastic component comprising at least one thermoplastic polymer and at least one water insensitive diluent having polar functionality; and at least one superabsorbent polymer.

2. The thermoplastic composition of claim 1 wherein said thermoplastic component is water insensitive.

3. The thermoplastic composition of claim 1 wherein said diluent is a plasticizer.

4. The thermoplastic composition of claim 1 wherein said diluent is a wax.

5. The thermoplastic composition of claim 1 wherein the diluent is present in an amount ranging from about 5 wt-% to about 30 wt-%.

6. The thermoplastic composition of claim 1 wherein the superabsorbent polymer is present in an amount ranging from about 30 wt% to about 60 wt-%.

7. The thermoplastic composition of claim 1 wherein the thermoplastic component comprises at least one polymer selected from the group consisting of block copolymers, amorphous polyolefins, crystalline polyolefins, interpolymers of ethylene and mixtures thereof.

8. The thermoplastic composition of claim 1 wherein the composition gels at a rate substantially equal to or faster than that of the superabsorbent polymer alone.

9. An article comprising a film layer disposed on a substrate, said film layer comprising the thermoplastic composition of claim 1.

10. The article of claim 9 wherein said superabsorbent polymer has a particle size equal to or greater than the thickness of the film layer.

11. A method of making a film comprising the steps of providing a molten mixture of a composition of claim 1 and forming a substantially continuous film from said molten mixture.

12. A nonwoven web comprising the composition of claim 1.

13. A disposable article comprising a body fluid pervious topsheet and a body fluid impervious backsheet and the composition of claim 1 disposed between said topsheet and backsheet.

14. A thermoplastic composition comprising a thermoplastic component comprising at least one interpolymer of ethylene having a melt index greater than about 100 g/10 minutes and a comonomer content greater than 30 wt-% and at least one superabsorbent polymer.

15. The thermoplastic composition of claim 14 wherein the melt index is greater than 400 g/10 min.

16. The thermoplastic composition of claim 14 wherein the melt index is greater than about 800 g/10 min.

17. The thermoplastic composition of claim 14 wherein the melt index is greater than about 1000 g/10 min.

18. The thermoplastic composition of claim 14 wherein the comonomer content is greater than about 33 wt-%.

19. The thermoplastic composition of claim 14 wherein the comonomer is selected from the group consisting of vinyl acetate, n-butyl acrylate, methacrylate and mixtures thereof.

20. A thermoplastic composition comprising about 25 wt-% to about 50 wt-% of a thermoplastic composition having a Brookfield viscosity of less than 30,000 cPs at about 180° C. and about 35 wt-% to about 75 wt-% of a superabsorbent polymer wherein the thermoplastic component consists essentially of:
   a) about 10 wt-% to about 50 wt-% of at least one water insoluble polymer;
   b) 5 wt-% to about 30 wt-% of a water insensitive plasticizer having polar functionality; and
   c) 0 wt-% to about 40 wt-% of a tackifier, wax, non-polar plasticizer, or a mixture thereof.

21. A method of applying superasborbent polymer to a substrate comprising the steps of:
   a) providing a molten mixture comprising the thermoplastic composition of claim 1; and
   b) applying said mixture to a substrate.

22. The method of claim 21 wherein said substrate is selected from the group consisting of, film, paper, nonwoven, tissue, and an absorbent core.

23. A thermoplastic composition comprising at thermoplastic component comprising at least one thermoplastic polymer and at least one water insensitive diluent having polar functionality and at least one superabsorbent polymer, said composition gelling at a rate substantially equal to or faster than that of the superabsorbent polymer alone.

24. A film layer disposed on a substrate, said film layer comprising a thermoplastic composition comprising at least one thermoplastic polymer and at least one water insensitive diluent having polar functionality and at least one superabsorbent polymer having a particle size equal to or greater than the thickness of the film.

* * * * *